United States Patent
Thuilliez et al.

(10) Patent No.: US 10,590,225 B2
(45) Date of Patent: Mar. 17, 2020

(54) USE OF A SILYLATED AROMATIC POLYPHENOL DERIVATIVE FOR THE PRODUCTION OF A PHENOL-ALDEHYDE RESIN FOR REINFORCEMENT OF A RUBBER COMPOSITION

(71) Applicant: COMPAGNIE GENERALE DES ETABLISSEMENTS MICHELIN, Clermont-Ferrand (FR)

(72) Inventors: Anne-Lise Thuilliez, Clermont-Ferrand (FR); Odile Gavard-Lonchay, Clermont-Ferrand (FR); Cedric Loubat, Castries (FR); Gilles Boutevin, Castries (FR)

(73) Assignee: COMPAGNIE GENERALE DES ETABLISSEMENTS MICHELIN, Clermont-Ferrand (FR)

(*) Notice: Subject to any disclaimer, the term of this patent is extended or adjusted under 35 U.S.C. 154(b) by 0 days.

(21) Appl. No.: 15/762,733

(22) PCT Filed: Sep. 23, 2016

(86) PCT No.: PCT/EP2016/072653
§ 371 (c)(1),
(2) Date: Mar. 23, 2018

(87) PCT Pub. No.: WO2017/050953
PCT Pub. Date: Mar. 30, 2017

(65) Prior Publication Data
US 2018/0273670 A1    Sep. 27, 2018

(30) Foreign Application Priority Data
Sep. 25, 2015 (FR) .................... 15 59070
Sep. 25, 2015 (FR) .................... 15 59073

(51) Int. Cl.
C08G 8/04 (2006.01)
C08G 16/02 (2006.01)
C07F 7/18 (2006.01)
C08G 59/00 (2006.01)
C08L 61/00 (2006.01)

(52) U.S. Cl.
CPC ............. *C08G 8/04* (2013.01); *C07F 7/1804* (2013.01); *C08G 16/0218* (2013.01); *C08G 59/00* (2013.01); *C08L 61/00* (2013.01)

(58) Field of Classification Search
CPC ..... C08F 8/04; C07F 7/18; C08G 8/04; C08G 16/0821
See application file for complete search history.

(56) References Cited

U.S. PATENT DOCUMENTS

| | | | |
|---|---|---|---|
| 3,336,349 A | 8/1967 | Voris | 260/410.5 |
| 3,462,468 A | 8/1969 | Taylor et al. | 260/410.5 |
| 3,600,431 A | 8/1971 | Taylor et al. | 260/479 R |
| 4,605,696 A | 8/1986 | Benko et al. | 524/432 |
| 4,683,241 A | 7/1987 | Miyano et al. | 514/512 |
| 5,021,522 A | 6/1991 | Durairaj et al. | 525/502 |
| 5,030,692 A | 7/1991 | Durairaj | 525/134 |
| 5,096,983 A | 3/1992 | Gerber | 525/506 |
| 5,208,274 A | 5/1993 | Gerber | 523/145 |
| 5,262,495 A | 11/1993 | Gerber | 525/506 |
| 5,310,811 A | 5/1994 | Cottman et al. | 525/305 |
| 7,199,175 B2 | 4/2007 | Vasseur | |
| 7,250,463 B2 | 7/2007 | Durel et al. | |
| 7,820,771 B2 | 10/2010 | Lapra et al. | |
| 7,900,667 B2 | 3/2011 | Vasseur | |
| 8,247,490 B1 | 8/2012 | Li | |
| 8,962,719 B2 | 2/2015 | Welter | 524/100 |
| 2003/0212185 A1 | 11/2003 | Vasseur | |
| 2005/0004297 A1 | 1/2005 | Durel et al. | |
| 2007/0112120 A1 | 5/2007 | Vasseur | |
| 2008/0132644 A1 | 6/2008 | Lapra et al. | |
| 2009/0270558 A1 | 10/2009 | Gandon-pain et al. | |
| 2012/0101211 A1 | 4/2012 | Fujiki et al. | 524/511 |
| 2013/0277609 A1 | 10/2013 | Goto et al. | 252/299.61 |
| 2014/0121308 A1 | 5/2014 | Welter | 524/81 |
| 2014/0200169 A1 | 7/2014 | Kilthau et al. | 508/278 |

(Continued)

FOREIGN PATENT DOCUMENTS

CN    101691419 A    4/2010
CN    103922981 A    7/2014
(Continued)

OTHER PUBLICATIONS

A. De Groot, et al., "Selective Cleavage of tert-Butyldimethylsilylethers ortho to a Carbonyl Group by Ultrasound," Tetrahedron, vol. 56, pp. 1541-1549 (2000).

J. Patra, et al., "Volatile Compounds and Antioxidant Capacity of the Bio-Oil Obtained by Pyrolysis of Japanese Red Pine (Pinus Densiflora Siebold and Zucc.)", Molecules, vol. 20, pp. 3986-4006 (2015).

F. Shirini, et al., "Nanocrystalline TiO2 as an Efficient and Reusable Catalyst for the Chemoselective Trimethylsilylation of Primary and Secondary Alcohols and Phenols," Chinese Chemical Letters, vol. 22, pp. 1211-1214 (2011).

(Continued)

*Primary Examiner* — Caixia Lu
(74) *Attorney, Agent, or Firm* — Venable LLP

(57) ABSTRACT

An aromatic polyphenol derivative comprising at least one aromatic ring bearing at least two —O—Z groups in the meta position relative to one another, the two positions ortho to at least one of the —O—Z groups being unsubstituted, is used for the manufacture of a phenol-aldehyde resin for reinforcing a rubber composition. Each —O—Z group represents an —O—Si($R_1R_2R_3$) group with $R_1$, $R_2$, $R_3$ representing, independently of one another, a hydrocarbon-based radical or a substituted hydrocarbon-based radical.

15 Claims, 4 Drawing Sheets

(56) References Cited

U.S. PATENT DOCUMENTS

| | | | |
|---|---|---|---|
| 2014/0235125 A1 | 8/2014 | Doisneau et al. | C09J 161/12 |
| 2015/0344784 A1 | 12/2015 | Goto et al. | 252/299.61 |
| 2017/0166010 A1 | 6/2017 | Michoud et al. | B60C 9/0007 |
| 2017/0362370 A1* | 12/2017 | Doisneau | C08G 8/04 |
| 2018/0009972 A1* | 1/2018 | Doisneau | B60C 1/00 |
| 2018/0016433 A1* | 1/2018 | Doisneau | B60C 1/00 |
| 2019/0077952 A1* | 3/2019 | Thuilliez | C08L 61/14 |

FOREIGN PATENT DOCUMENTS

| | | |
|---|---|---|
| DE | 10 2011 102 540 A1 | 11/2012 |
| EP | 0 311 371 A2 | 4/1989 |
| EP | 2 727 957 A1 | 5/2014 |
| FR | 3 017 133 A1 | 8/2015 |
| GB | 470 397 | 8/1937 |
| GB | 1 352 870 A | 5/1974 |
| GB | 2140017 A | 11/1984 |
| JP | 2012-92179 | 5/2012 |
| JP | 2014-111786 | 6/2014 |
| WO | 97/36724 A2 | 10/1997 |
| WO | 99/16600 A1 | 4/1999 |
| WO | 02/10269 A1 | 2/2002 |
| WO | 03/016387 A1 | 2/2003 |
| WO | 2006/069792 A1 | 7/2006 |
| WO | 2006/069793 A1 | 7/2006 |
| WO | 2009/155747 A1 | 12/2009 |
| WO | 2013/017422 A1 | 2/2013 |

OTHER PUBLICATIONS

M. Moghadam, et al., "[SnIV(TPP)(BF4)2]: An Efficient and Reusable Catalyst for Chemoselective Trimethylsilylation of Alcohols and Phenols with Hexamethyldisilazane," Polyhedron, vol. 29, pp. 212-219 (2010).

M. Miyano, et al., "(Acyloxy)benzophenones and (Acyloxy)-4-pyrones. A New Class of Inhibitors of Human Neutrophil Elastase," J. Med. Chem., vol. 31, pp. 1052-1061 (1988).

Co-pending U.S. Appl. No. 15/762,663, filed Sep. 23, 2016.

* cited by examiner

USE OF A SILYLATED AROMATIC POLYPHENOL DERIVATIVE FOR THE PRODUCTION OF A PHENOL-ALDEHYDE RESIN FOR REINFORCEMENT OF A RUBBER COMPOSITION

FIELD OF THE INVENTION

The invention relates to the use of an aromatic polyphenol derivative for the manufacture of a phenol-aldehyde resin for reinforcing a rubber composition.

RELATED ART

It is known to use, in some parts of the tyres, rubber compositions having high stiffness during small strains of the tyre. Resistance to small strains is one of the properties which a tyre must have in order to respond to the stresses to which it is subjected.

High stiffness may be obtained using what is referred to as a concentrated to vulcanization system, that is to say especially comprising relatively high contents of sulfur and of vulcanization accelerator.

Nonetheless, such a concentrated vulcanization system detrimentally affects the uncured ageing of the composition. Thus, when the composition is in the form of a semi-finished product, for example of a rubber strip, the sulfur may migrate to the surface of the semi-finished product. This phenomenon, referred to as blooming, leads to a detrimental effect on the green tack of the semi-finished product during prolonged storage thereof, with, as consequence, degradation of the adhesion between the semi-finished products during manufacture of the tyre.

Moreover, storage of the uncured composition containing a concentrated vulcanization system is liable to lead to a reduction in the delay phase of the composition during vulcanization thereof, that is to say the time preceding the start of vulcanization. Consequently, the composition may begin to cure prematurely in certain forming tools and the vulcanization kinetics are liable to be altered and the vulcanization efficiency to be reduced.

Such a concentrated vulcanization system also detrimentally affects ageing in the cured state. Indeed, degradation of the mechanical properties of the cured composition is observed, especially at the limits, for example of the elongation at break.

High stiffness may otherwise be obtained by increasing the content of reinforcing filler.

Nonetheless, in a known way, increasing the stiffness of a rubber composition by increasing the content of filler may detrimentally affect the hysteresis properties and thus the rolling resistance properties of tyres. However, it is an ongoing aim to lower the rolling resistance of tyres in order to reduce the consumption of fuel and thus to protect the environment.

Finally, high stiffness may be obtained by incorporating certain reinforcing resins, as disclosed in WO 02/10269.

Conventionally, the increase in stiffness is obtained by incorporating reinforcing resins based on a methylene acceptor/donor system. The terms "methylene acceptor" and "methylene donor" are well known to those skilled in the art and are widely used to denote compounds capable of reacting together to generate, by condensation, a three-dimensional reinforcing resin which will become superimposed and interpenetrated with the reinforcing filler/elastomer network, on the one hand, and with the elastomer/sulfur network, on the other hand (if the crosslinking agent is sulfur).

The methylene acceptor is combined with a hardener, capable of crosslinking or curing it, also commonly known as a methylene donor. Examples of such methylene acceptors and donors are described in WO 02/10269.

The methylene donors conventionally used in rubber compositions for tyres are hexamethylenetetramine (abbreviated to HMT) or hexamethoxymethylmelamine (abbreviated to HMMM or H3M) or hexaethoxymethylmelamine.

The methylene acceptors conventionally used in rubber compositions for tyres are pre-condensed phenolic resins.

Nonetheless, the combination of phenolic resin conventionally used as methylene acceptor, with HMT or H3M as methylene donor, produces formaldehyde during the vulcanization of the rubber composition. However, it is desirable to reduce, or even eliminate in the long run, formaldehyde from rubber compositions due to the environmental impact of these compounds and the recent developments in regulations, especially European regulations, relating to this type of compound.

SUMMARY OF THE INVENTION

The objective of the invention is to make it possible to reinforce rubber compositions by means of low-environmental-impact compounds.

For this purpose, one subject of the invention is the use of an aromatic polyphenol derivative comprising at least one aromatic ring bearing at least two —O—Z groups in the meta position relative to one another, the two positions ortho to at least one of the —O—Z groups being unsubstituted, and in which each —O—Z group represents an —O—Si($R_1R_2R_3$) group with $R_1$, $R_2$, $R_3$ representing, independently of one another, a hydrocarbon-based radical or a substituted hydrocarbon-based radical, for the manufacture of a phenol-aldehyde resin for reinforcing a rubber composition.

The combination of the aromatic polyphenol derivative and of the aldehyde makes it possible to obtain rubber compositions having an equivalent or even vastly improved stiffness at low strain compared to conventional rubber compositions which comprise the methylene donors HMT or H3M and compared to the rubber compositions devoid of reinforcing resin, and therefore to reinforce the rubber composition in which the reinforcing phenol-aldehyde resin is manufactured or formed (the two terms being equivalent) during the crosslinking of the rubber composition.

In accordance with the invention, the reinforcing phenol-aldehyde resin is based on the aromatic polyphenol derivative and on an aldehyde and is manufactured in situ, by crosslinking, in the rubber composition, especially during the crosslinking of this rubber composition, for example by vulcanizing or curing.

The Applicants have discovered, during their research, that the aromatic polyphenol derivatives according to the invention advantageously make it possible to avoid a premature crosslinking of a phenol-aldehyde resin based on this aromatic polyphenol derivative and on an aldehyde. Specifically, one problem linked to the use of certain reinforcing resins, especially those based on the aromatic polyphenol and on the aldehyde, is their ability to crosslink prematurely. Indeed, after the step of manufacturing the composition comprising the constituents of these reinforcing resins based on the corresponding aromatic polyphenol and on the corresponding aldehyde, the composition is shaped for example by calendering, for example in the form of a sheet or a slab, or else is extruded, for example to form a rubber profiled element. Yet, due to their ability to crosslink rapidly, these reinforcing resins based on the corresponding aromatic polyphenol and on the corresponding aldehyde crosslink and stiffen the composition, which may hamper the shaping of the rubber composition.

In fact, the aromatic polyphenol derivative and the aldehyde react less quickly than the corresponding aromatic polyphenol and the corresponding aldehyde. This rate of reaction may be determined by measuring the change in the rheometric torque as a function of the time. This change describes the stiffening of the composition following in particular the crosslinking of the phenol-aldehyde resin. From the comparison of the change in the rheometric torques of a first composition comprising the aromatic polyphenol derivative and the aldehyde and of a second composition comprising the corresponding aromatic polyphenol and the corresponding aldehyde, it is seen that the aromatic polyphenol derivative makes it possible to delay the crosslinking of the phenol-aldehyde resin relative to the direct reaction between the aromatic polyphenol and the aldehyde.

The inventors behind the invention put forward the hypothesis that the aromatic polyphenol derivative according to the invention is a precursor of the corresponding aromatic polyphenol and that the latter makes it possible to avoid a premature crosslinking of the phenol-aldehyde resin due to the Z radical of each —O—Z group which is other than hydrogen. Specifically, the Z radical of each —O—Z group would act as a temporary protective group enabling, according to the hypothesis of the inventors, the formation of a hydroxyl function under predetermined reaction conditions and therefore the formation of the corresponding aromatic polyphenol. The predetermined reaction conditions under which this formation is possible depend on several parameters such as the pressure, the temperature or else the chemical species present in the reaction medium. These reaction conditions depend on the —O—Z group and are easily determinable, or even known by a person skilled in the art. For example, such reaction conditions are the heating of the rubber composition to a temperature greater than or equal to 80° C., preferably to 100° C. and more preferentially to 120° C.

Thus, the aromatic polyphenol derivative according to the invention and the aldehyde may react less quickly than the corresponding aromatic polyphenol and the corresponding aldehyde. This rate of reaction may be determined by measuring the change in the rheometric torque as a function of the time. This change describes the stiffening of the composition following in particular the crosslinking of the phenol-aldehyde resin. From the comparison of the change in the rheometric torques of a first composition comprising the aromatic polyphenol derivative according to the invention and the aldehyde and of a second composition comprising the corresponding aromatic polyphenol and the corresponding aldehyde, it is seen that the aromatic polyphenol derivative according to the invention makes it possible to delay the crosslinking of the phenol-aldehyde resin relative to the direct reaction between the aromatic polyphenol and the aldehyde.

The —O—Z group is such that the reaction between the aromatic polyphenol derivative according to the invention and the aldehyde enables the crosslinking of a phenol-aldehyde resin. Preferably, the —O—Z group is such that the reaction between the aromatic polyphenol derivative according to the invention and the aldehyde enables the crosslinking of a phenol-aldehyde resin under the same reaction conditions, preferably the same temperature reaction conditions, as a phenol-aldehyde resin based on the corresponding aromatic polyphenol (comprising hydroxyl groups instead of —O—Z groups) and on the same aldehyde. Conventionally, the temperature is greater than or equal to 120° C., preferably greater than or equal to 140° C.

Furthermore, the specific combination of the aldehyde and of the aromatic polyphenol derivative according to the invention makes it possible to obtain excellent stiffness retention of the rubber composition with the increase in temperature, this retention being greater, in most embodiments, than that of rubber compositions devoid of reinforcing resin. The specific combination of the aldehyde and of this aromatic polyphenol derivative also makes it possible to obtain excellent stiffness retention of the rubber composition with the increase in temperature, this retention being equivalent, or even greater in certain embodiments, than that of conventional rubber compositions that comprise HMT or H3M methylene donors. As already explained above, the inventors behind the invention put forward the hypothesis that the aromatic polyphenol derivative according to the invention (comprising hydroxyl groups instead of —O—Z groups) is a precursor of the corresponding aromatic polyphenol. As already explained above, this makes it possible to avoid an immediate crosslinking of the phenol-aldehyde resin owing to a reaction that would generate, after a delay, the hydroxyl function or functions from the aromatic polyphenol derivative (comprising hydroxyl groups instead of —O—Z groups). Specifically, the —O—Z groups would act as temporary protective groups enabling, according to the hypothesis of the inventors, the formation of hydroxyl functions under predetermined reaction conditions (in other words the regeneration of the aromatic polyphenol corresponding to the derivative). The time taken to regenerate the aromatic polyphenol, even when it is very short, for example of the order of a minute, would enable a better dispersion of the aldehyde and of the aromatic polyphenol derivative (comprising hydroxyl groups instead of —O—Z groups) in the reaction mixture which would make it possible to obtain a phenol-aldehyde resin having a more homogeneous crosslinking and therefore a better temperature resistance of the phenol-aldehyde resin.

The name "aromatic polyphenol derivative" is used due to the structural similarity existing between this compound referred to as "aromatic polyphenol derivative" and the corresponding aromatic polyphenol. Specifically, the aromatic polyphenol derivative is a compound having a structure analogous to that of the corresponding aromatic polyphenol but in which the hydrogen of at least two hydroxyl functions is replaced by the Z radical.

It is thus possible to define a general formula (W) for the aromatic polyphenol derivative according to the invention represented below:

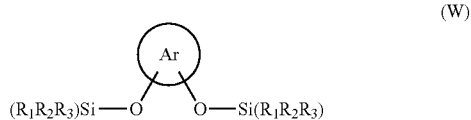

(W)

in which Ar is the aromatic ring.

An aromatic polyphenol derivative according to the invention should not be understood as meaning that it can be a pre-condensed resin which would comprise hydroxyl functions enabling the reaction with the aldehyde. In certain preferential embodiments, all the —O—Z groups are identical. However, in other embodiments, at least two —O—Z groups are different.

As temporary protective group, each —O—Z group is preferentially devoid of a function that is reactive with respect to the aldehyde. In the various embodiments described, each $R_1$, $R_2$ and $R_3$ radical is preferentially devoid of a function that is reactive with respect to the aldehyde.

As temporary protective group, each —O—Z group is preferentially devoid of a function that is reactive with respect to the other constituents of the rubber composition. In the various embodiments described, each $R_1$, $R_2$ and $R_3$ radical is preferentially devoid of a function that is reactive with respect to the other constituents of the rubber composition.

A reactive function is understood here to mean a function that would react under reaction conditions necessary for the regeneration of the aromatic polyphenol and under reaction conditions necessary for the crosslinking of the phenol-aldehyde resin.

Preferably, the molar mass of each —O—Z group is less than or equal to 1000 g·mol$^{-1}$. Typically, the molar mass of each —O—Z group is between 15 g·mol$^{-1}$ and 1000 g·mol$^{-1}$, preferentially between 15 g·mol$^{-1}$ and 500 g·mol$^{-1}$.

"Meta position relative to one another" is intended to mean that the —O—Z groups are borne by carbons of the aromatic ring which are separated from one another by a single other carbon of the aromatic ring.

"Position ortho to a group" is intended to mean the position occupied by the carbon of the aromatic ring which is immediately adjacent to the carbon of the aromatic ring bearing the group.

Within the context of the invention, the carbon-based products mentioned in the description may be of fossil or biobased origin. In the latter case, they may partially or completely result from biomass or be obtained from renewable starting materials resulting from biomass.

The expression "resin based on" should, of course, be understood as meaning a resin comprising the mixture and/or the reaction product of the various base constituents used for this resin, it being possible for some of them to be intended to react or capable of reacting with one another or with their immediate chemical surroundings, at least partly, during the various phases of the method for manufacturing the composition, the composites or the tyre, in particular during a curing stage. Thus, provision could also be made for the aldehyde to be derived from a precursor of this aldehyde. For example, should formaldehyde be used as aldehyde, a precursor of the formaldehyde would be hexamethylenetetramine (HMT).

Thus, the invention makes it possible to manufacture a rubber composition comprising at least one phenol-aldehyde resin based on at least one aromatic polyphenol derivative according to the invention and on at least one aldehyde.

The invention also makes it possible to manufacture a rubber composition comprising at least one aromatic polyphenol derivative according to the invention and at least one aldehyde.

The invention may also make it possible to carry out a method for manufacturing a rubber composition, comprising a step of mixing at least one aromatic polyphenol derivative according to the invention and at least one aldehyde.

Preferably, during the mixing step, at least one elastomer is also mixed into the composition.

The invention may also make it possible to carry out a method for manufacturing a rubber composition in the cured state, comprising:

a step of manufacturing a rubber composition in the uncured state, comprising a step of mixing at least one aromatic polyphenol derivative according to the invention and at least one aldehyde, then, a step of shaping the rubber composition in the uncured state, then, a step of vulcanizing the rubber composition during which a phenol-aldehyde resin based on the aromatic polyphenol derivative according to the invention and on the aldehyde is crosslinked.

Alternatively, the step of crosslinking by vulcanizing or curing may be replaced by a step of crosslinking using a crosslinking system other than sulfur.

As explained above, the inventors put forward the hypothesis according to which, during the crosslinking step, for example by vulcanizing or curing, the following are carried out, prior to the crosslinking of the phenol-aldehyde resin:

a step of forming an aromatic polyphenol from the aromatic polyphenol derivative according to the invention by formation, on the aromatic ring, of at least two hydroxyl functions in the meta position relative to one another, the two positions ortho to at least one of the hydroxyl functions being unsubstituted, each hydroxyl function being obtained from each —O—Z group, and a step of crosslinking the phenol-aldehyde resin starting from the aromatic polyphenol and the aldehyde.

Thus, the use of the aromatic polyphenol derivative according to the invention also makes it possible to obtain rubber compositions having a vastly improved stiffness at low strain compared to conventional rubber compositions.

Rubber composition is intended to mean that the composition comprises at least one elastomer or a rubber (the two terms being synonyms) and at least one other component. A rubber composition thus comprises a matrix of elastomer or of rubber in which at least the other component is dispersed. A rubber composition is in a plastic state in the uncured (non-crosslinked) state and in an elastic state in the cured (crosslinked) state, but never in a liquid state. A rubber composition must not be confused with an elastomer latex, which is a composition in a liquid state comprising a liquid solvent, generally water, and at least one elastomer or a rubber dispersed in the liquid solvent so as to form an emulsion. Thus, the rubber composition is not an aqueous adhesive composition.

The rubber composition thus comprises at least one (that is to say, one or more) phenol-aldehyde resin; this phenol-aldehyde resin being based on at least one (that is to say, one or more) aldehyde and at least one (that is to say, one or more) aromatic polyphenol derivative according to the invention, which constituents will be described in detail below.

In the present description, unless expressly indicated otherwise, all the percentages (%) shown are percentages by weight. The acronym "phr" signifies parts by weight per hundred parts of elastomer.

Furthermore, any range of values denoted by the expression "between a and b" represents the range of values extending from more than a to less than b (in other words excluding the limits a and b), whereas any range of values denoted by the expression "from a to b" means the range of values extending from the limit "a" as far as the limit "b", in other words including the strict limits "a" and "b".

DETAILED DESCRIPTION OF THE INVENTION

Figure 1:
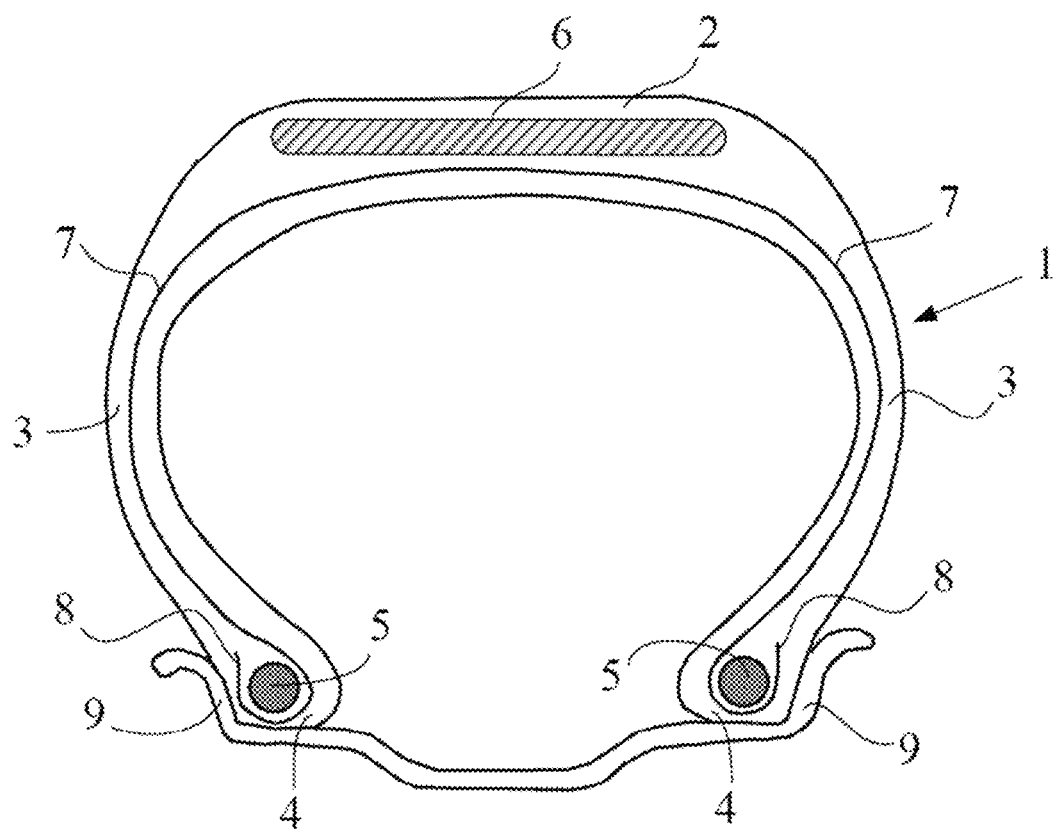
FIG. 1 is a schematic drawing of a radial section of a tire in accordance with the invention.

Use of the Aromatic Polyphenol Derivative According to the Invention

The aromatic polyphenol derivative according to the invention comprises at least one aromatic ring bearing at least two —O—Z groups in the meta position relative to one another, the two positions ortho to at least one of these —O—Z groups being unsubstituted.

In one embodiment of the invention, the aromatic polyphenol derivative is used to generate a delay phase during the crosslinking of a phenol-aldehyde resin based on the aromatic polyphenol derivative and on an aldehyde, for example as described below.

In another embodiment, the aromatic polyphenol derivative is used in a phenol-aldehyde resin to maintain the stiffness of a rubber composition with the increase in the temperature.

In accordance with the invention, the aromatic polyphenol derivative may be, in one embodiment, a simple aromatic polyphenol derivative molecule comprising one or more aromatic rings, at least one of these aromatic rings, or even each aromatic ring, bearing at least two —O—Z groups in the meta position relative to one another, the two positions ortho to at least one of these —O—Z groups being unsubstituted.

Such simple molecules do not comprise a repeat unit.

In accordance with the invention, the aromatic polyphenol derivative may be, in another embodiment, a pre-condensed resin based:

on at least one aromatic polyphenol comprising at least one aromatic ring bearing at least two hydroxyl functions in the meta position relative to one another, the two positions ortho to at least one of the hydroxyl functions being unsubstituted; and on at least one compound comprising at least one aldehyde function, the hydroxyl functions of the pre-condensed resin that are free at the end of the condensation of the pre-condensed resin being substituted by —O—Z groups.

Such a pre-condensed resin based on aromatic polyphenol is in accordance with the invention and comprises, unlike the simple molecule described above, a repeat unit. In this case, the repeat unit comprises at least one aromatic ring bearing at least two —O—Z groups in the meta position relative to one another, the two positions ortho to at least one of these —O—Z groups being unsubstituted. In this embodiment, in order to form the aromatic polyphenol derivative in pre-condensed resin form, the pre-condensed resin based on an aromatic polyphenol comprising at least one aromatic ring bearing at least two —OH hydroxyl functions in the meta position relative to one another, the two positions ortho to at least one of the —OH hydroxyl functions being unsubstituted, is formed and this pre-condensed resin is reacted with a compound that makes it possible to form the —O—Z group from each hydroxyl function left free at the end of the condensation of the pre-condensed resin.

In another embodiment, the aromatic polyphenol derivative is a mixture of a derivative of an aromatic polyphenol forming a simple molecule and of a pre-condensed resin based on aromatic polyphenol in which the hydroxyl functions of the pre-condensed resin that are free at the end of the condensation of the pre-condensed resin are substituted by —O—Z groups.

In the particular embodiments that follow, the aromatic ring or rings of the aromatic polyphenol derivative are described. For the sake of clarity, the "derivative of the aromatic polyphenol" is described therein in its simple molecule form. The aromatic polyphenol at the origin of the corresponding derivatives could then be condensed and will in part define the repeat unit. The characteristics of the pre-condensed resin are described in greater detail below.

Advantageously, each $R_1$, $R_2$, $R_3$ group represents, independently of one another, a radical selected from the group consisting of alkyl, aryl, arylalkyl, alkylaryl, cycloalkyl and alkenyl radicals.

Preferentially, each $R_1$, $R_2$, $R_3$ group represents, independently of one another, a radical selected from the group consisting of methyl, ethyl, propyl, phenyl, allyl and vinyl radicals.

Even more preferentially, each $R_1$, $R_2$, $R_3$ group represents, independently of one another, a radical selected from the group consisting of methyl, ethyl, propyl, butyl, allyl and vinyl radicals.

In the preceding embodiments, the propyl radicals comprise the radicals of formula —$C_3H_7$. These radicals are n-propyl and isopropyl.

In the preceding embodiments, the butyl radicals comprise the radicals of formula —$C_4H_9$. These radicals are n-butyl, isobutyl, sec-butyl and tert-butyl.

In the preceding embodiments, the aryl radicals comprise the aromatic rings from which a hydrogen atom has been removed. For example, the aryl radical is the $C_6H_5$ radical obtained from benzene $C_6H_6$. Another example of an aryl radical is the $C_4H_3O$ radical obtained from furan $C_4H_4O$.

In a preferred embodiment, the aromatic ring bears three —O—Z groups in the meta position relative to one another.

The two positions ortho to each —O—Z group are preferably unsubstituted. This is intended to mean that the two carbon atoms located on either side of (in the position ortho to) the carbon atom bearing the —O—Z group just bear a hydrogen atom.

Even more preferentially, the remainder of the aromatic ring is unsubstituted. This is intended to mean that the other carbon atoms of the remainder of the aromatic ring (those other than the carbon atoms bearing —O—Z groups) just bear a hydrogen atom.

In one embodiment, the aromatic polyphenol derivative comprises several aromatic rings, at least two of these each bearing at least two —O—Z groups in the meta position relative to one another, the two positions ortho to at least one of the —O—Z groups of at least one aromatic ring being unsubstituted.

In a preferred embodiment, at least one of the aromatic rings bears three —O—Z groups in the meta position relative to one another.

The two positions ortho to each —O—Z group of at least one aromatic ring are preferably unsubstituted.

Even more preferentially, the two positions ortho to each —O—Z group of each aromatic ring are unsubstituted.

Advantageously, the, or each, aromatic ring is a benzene ring.

Mention may in particular be made, as examples of aromatic polyphenol derivatives according to the invention comprising just one aromatic ring, of the derivatives of resorcinol and of phloroglucinol, of structural formulae:

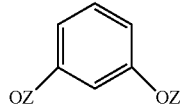
(I)

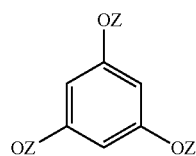
(II)

By way of example, in the case in which the aromatic polyphenol derivative according to the invention comprises several aromatic rings, at least two of these aromatic rings, which are identical or different, are selected from those of general formulae:

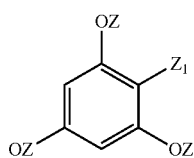
(III-a)

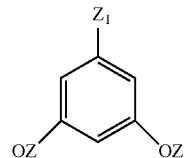
(III-b)

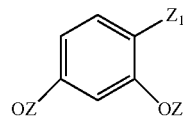
(III-c)

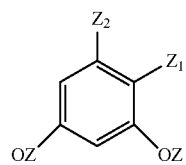
(III-d)

in which the $Z_1$ and $Z_2$ symbols, which are identical or different, if there are several of them on the same aromatic ring, represent an atom (for example, carbon, sulfur or oxygen) or a connecting group, by definition at least divalent, which connects at least these two aromatic rings to the remainder of the aromatic polyphenol derivative.

Another example of aromatic polyphenol derivative according to the invention is a derivative of 2,2',4,4'-tetrahydroxydiphenyl sulfide, a derivative that has the following structural formula:

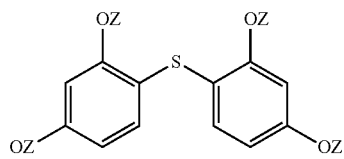
(IV)

Another example of aromatic polyphenol derivative according to the invention is a derivative of 2,2',4,4'-tetrahydroxydiphenyl benzophenone, a derivative of the following structural formula:

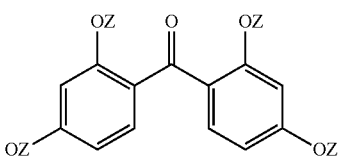
(V)

It is noted that each aromatic polyphenol derivative IV and V is an aromatic polyphenol derivative according to the invention comprising two aromatic rings (of formulae III-c), each of which bears at least two (in this instance two) —O—Z groups in the meta position relative to one another.

It is noted, in the case of an aromatic polyphenol derivative according to the invention comprising at least one aromatic ring in accordance with formula III-b, that the two positions ortho to each —O—Z group of at least one aromatic ring are unsubstituted. In the case of an aromatic polyphenol derivative according to the invention comprising several aromatic rings in accordance with formula III-b, the two positions ortho to each —O—Z group of each aromatic ring are unsubstituted.

According to one embodiment of the invention, the aromatic polyphenol derivative according to the invention is selected from the group consisting of the aromatic polyphenol derivatives of formulae (I), (II), (IV) and (V) described above and also the mixtures of these aromatic polyphenol derivatives. In a particularly advantageous embodiment, the aromatic polyphenol derivative according to invention is the aromatic polyphenol derivative (II).

In one embodiment, the aromatic polyphenol derivative comprises a pre-condensed resin based on at least one aromatic polyphenol as described in any one of the embodiments described in the present application, the hydroxyl functions of the pre-condensed resin that are free at the end of the condensation of the pre-condensed resin being substituted by —O—Z groups.

This pre-condensed resin is advantageously based:

on at least one aromatic polyphenol as defined above, and preferentially selected from the group consisting of resorcinol, phloroglucinol, 2,2',4,4'-tetrahydroxydiphenyl sulfide, 2,2',4,4'-tetrahydroxybenzophenone and the mixtures thereof; and on at least one compound comprising at least one aldehyde function.

The compound that comprises at least one aldehyde function and that reacts with said aromatic polyphenol may be an aldehyde as defined below. Advantageously, said compound comprising at least one aldehyde function is selected from the group consisting of formaldehyde, benzaldehyde, furfuraldehyde, 2,5-furandicarboxaldehyde, 1,4- benzenedicarboxaldehyde, 1,3-benzenedicarboxaldehyde, 1,2-benzenedicarboxaldehyde and the mixtures of these compounds.

Thus, in the pre-condensed resin based on aromatic polyphenol, the repeat unit comprises at least one aromatic ring bearing at least two hydroxyl functions in the meta position relative to one another, at least one of the carbon atoms of the aromatic ring, which was unsubstituted before the condensation of the pre-condensed resin, being connected to another unit.

Irrespective of the compound other than the aromatic polyphenol at the heart of the pre-condensed resin, this pre-condensed resin is devoid of free formaldehyde. Specifically, even in the case where the pre-condensed resin is based on an aromatic polyphenol as described previously and on formaldehyde, since the formaldehyde has already reacted with the aromatic polyphenol, the pre-condensed resin is devoid of free formaldehyde liable to be able to react with an aldehyde in accordance with the invention in a subsequent step.

The aromatic polyphenol derivative may also comprise a mixture of a free aromatic polyphenol derivative molecule and of a pre-condensed resin based on aromatic polyphenol, the hydroxyl functions of the pre-condensed resin that are free at the end of the condensation of the pre-condensed resin being substituted by —O—Z groups. In particular, the aromatic polyphenol derivative may also comprise a mixture of a derivative of phloroglucinol and of a pre-condensed resin based on phloroglucinol, the hydroxyl functions of the pre-condensed resin that are free at the end of the condensation of the pre-condensed resin being substituted by —O—Z groups.

The definitions of the —O—Z group which follow apply equally to the aromatic polyphenol derivative in its simple molecule or pre-condensed resin form.

Rubber Composition

Depending on the use of the composition, an amount of aldehyde ranging from 0.1 to 25 phr will be used. Likewise, an amount of aromatic polyphenol derivative according to the invention ranging from 0.1 to 25 phr will be used.

In certain embodiments, the [aldehyde]:[aromatic polyphenol derivative] molar ratio advantageously varies from 3:1 to 1:1, advantageously from 3:1 to 1.5:1.

Depending on the use that is made of the composition, the rubber composition has, in the cured state, a secant modulus at 10% elongation, MA10, measured according to standard ASTM D 412, 1998 (test specimen C) of greater than or equal to 10 MPa, preferably greater than or equal to 20 MPa, preferentially greater than or equal to 30 MPa, more preferentially greater than or equal to 40 MPa and even more preferentially greater than or equal to 60 MPa.

The rubber composition preferably comprises a diene elastomer.

An elastomer or rubber (the two terms being synonyms) of the "diene" type is intended to mean, generally, an elastomer resulting at least in part (i.e., a homopolymer or a copolymer) from diene monomers (monomers bearing two conjugated or unconjugated carbon-carbon double bonds).

Particularly preferentially, the diene elastomer of the rubber composition is selected from the group consisting of polybutadienes (BRs), synthetic polyisoprenes (IRs), natural rubber (NR), butadiene copolymers, isoprene copolymers and the mixtures of these elastomers. Such copolymers are more preferentially selected from the group consisting of butadiene/styrene copolymers (SBRs), isoprene/butadiene copolymers (BIRs), isoprene/styrene copolymers (SIRs), isoprene/butadiene/styrene copolymers (SBIRs) and the mixtures of such copolymers.

The rubber compositions may contain just one diene elastomer or a mixture of several diene elastomers, it being possible for the diene elastomer or elastomers to be used in combination with any type of synthetic elastomer other than a diene elastomer, or even with polymers other than elastomers, for example thermoplastic polymers.

The rubber composition preferably comprises a reinforcing filler.

When a reinforcing filler is used, use may be made of any type of reinforcing filler known for its abilities to reinforce a rubber composition which can be used for the manufacture of tyres, for example an organic filler, such as carbon black, a reinforcing inorganic filler, such as silica, or else a blend of these two types of filler, especially a blend of carbon black and silica.

All the carbon blacks conventionally used in tyres ("tyre-grade" blacks) are suitable as carbon blacks. Mention will more particularly be made, for example, of the reinforcing carbon blacks of the 100, 200 or 300 series (ASTM grades).

In the case of the use of carbon blacks with an isoprene elastomer, the carbon blacks might, for example, be already incorporated in the isoprene elastomer in the form of a masterbatch (see, for example, applications WO 97/36724 or WO 99/16600).

Mention may be made, as examples of organic fillers other than carbon blacks, of functionalized polyvinylaromatic organic fillers, such as described in applications WO-A-2006/069792 and WO-A-2006/069793.

"Reinforcing inorganic filler" should be understood, in the present application, by definition, as meaning any inorganic or mineral filler, regardless of its colour and its origin (natural or synthetic), also referred to as "white filler", "clear filler" or even "non-black filler", in contrast to carbon black, capable of reinforcing by itself alone, without means other than an intermediate coupling agent, a rubber composition intended for the manufacture of tyres, in other words capable of replacing, in its reinforcing role, a conventional tyre-grade carbon black. Such a filler is generally characterized, in a known way, by the presence of hydroxyl (—OH) groups at its surface.

The physical state in which the reinforcing inorganic filler is provided is not important, whether it is in the form of a powder, of micropearls, of granules, of beads or any other appropriate densified form. Of course, reinforcing inorganic filler is also intended to mean mixtures of different reinforcing inorganic fillers, in particular of highly dispersible siliceous and/or aluminous fillers as described below.

Mineral fillers of the siliceous type, in particular silica ($SiO_2$), or of the aluminous type, in particular alumina ($Al_2O_3$), are especially suitable as reinforcing inorganic fillers. The silica used may be any reinforcing silica known to those skilled in the art, especially any precipitated or fumed silica having a BET surface area and a CTAB specific surface area both of less than 450 $m^2/g$, preferably from 30 to 400 $m^2/g$. Mention will be made, as highly dispersible precipitated silicas ("HDSs"), for example, of the Ultrasil 7000 and Ultrasil 7005 silicas from Evonik, the Zeosil 1165MP, 1135MP and 1115MP silicas from Rhodia, the Hi-Sil EZ150G silica from PPG, the Zeopol 8715, 8745 and 8755 silicas from Huber or the silicas with a high specific surface area as described in application WO 03/16837.

Finally, those skilled in the art will understand that, as filler equivalent to the reinforcing inorganic filler described in the present section, use might be made of a reinforcing filler of another, especially organic, nature, provided that this reinforcing filler is covered with an inorganic layer, such as silica, or else comprises functional sites, especially hydroxyl sites, at its surface which require the use of a coupling agent in order to establish the bond between the filler and the elastomer.

The content of total reinforcing filler (carbon black and/or reinforcing inorganic filler, such as silica) is preferably within a range extending from 5 to 120 phr, more preferentially from 5 to 100 phr and even more preferentially from 5 to 90 phr.

The carbon black can advantageously constitute the sole reinforcing filler or the predominant reinforcing filler. Of course, it is possible to use just one carbon black or a blend of several carbon blacks of different ASTM grades. The carbon black can also be used as a blend with other reinforcing fillers and in particular reinforcing inorganic fillers as described above, and in particular silica.

When an inorganic filler (for example silica) is used in the rubber composition, alone or as a blend with carbon black, its content is within a range from 0 to 70 phr, preferentially from 0 to 50 phr, in particular also from 5 to 70 phr, and even more preferentially this proportion varies from 5 to 50 phr, particularly from 5 to 40 phr.

The rubber composition preferably comprises various additives.

The rubber compositions may also comprise all or some of the standard additives customarily used in the elastomer compositions intended for the manufacture of tyres, such as for example plasticizers or extending oils, whether the latter are aromatic or non-aromatic in nature, pigments, protective agents, such as antiozone waxes, chemical antiozonants, antioxidants, antifatigue agents or else adhesion promoters.

The rubber composition preferably comprises a crosslinking system, more preferentially a vulcanization system.

The vulcanization system comprises a sulfur-donating agent, for example sulfur.

The vulcanization system preferably comprises vulcanization activators, such as zinc oxide and stearic acid.

The vulcanization system preferably comprises a vulcanization accelerator and/or a vulcanization retarder.

The sulfur or sulfur-donating agent is used at a preferential content within a range from 0.5 to 10 phr, more preferentially within a range from 0.5 to 8.0 phr. The combined vulcanization accelerators, retarders and activators are used at a preferential content within a range from 0.5 to 15 phr. The vulcanization activator or activators is or are used at a preferential content within a range from 0.5 to 12 phr.

The crosslinking system proper is preferentially based on sulfur and on a primary vulcanization accelerator, in particular on an accelerator of the sulfenamide type. Additional to this vulcanization system are various known secondary vulcanization accelerators or vulcanization activators, such as zinc oxide, stearic acid, guanidine derivatives (in particular diphenylguanidine), etc.

Use may be made, as (primary or secondary) accelerator, of any compound capable of acting as accelerator of the vulcanization of diene elastomers in the presence of sulfur, especially accelerators of the thiazole type and their derivatives and accelerators of the thiuram and zinc dithiocarbamate types. These accelerators are more preferentially selected from the group consisting of 2-mercaptobenzothiazole disulfide (abbreviated to "MBTS"), N-cyclohexyl-2-benzothiazolesulfenamide (abbreviated to "CBS"), N,N-dicyclohexyl-2-benzothiazolesulfenamide (abbreviated to "DCBS"), N-(tert-butyl)-2-benzothiazolesulfenamide (abbreviated to "TBBS"), N-(tert-butyl)-2-benzothiazolesulfenimide (abbreviated to "TBSI"), zinc dibenzyldithiocarbamate (abbreviated to "ZBEC") and the mixtures of these compounds. Use is preferably made of a primary accelerator of the sulfenamide type.

In one embodiment, the rubber composition is in the cured state, i.e. vulcanized. In other embodiments, the composition is in the uncured state, i.e. unvulcanized, the crosslinked phenol-aldehyde resin having been added subsequently to the unvulcanized composition.

In certain embodiments, the composition comprises a residue obtained from the —Z radical of each —O—Z group. Prior to the crosslinking of the resin, and as assumed by the inventors behind the invention, after forming each —OH hydroxyl function, each Z radical of each —O—Z group may make it possible to obtain a residue generated in situ. Certain residues remain permanently in the composition and, where appropriate, may be used for some of the properties thereof.

In other embodiments, the residue generated only remains temporarily in the composition either because it spontaneously leaves therefrom under the conditions for manufacturing the composition, for example in the form of gas, especially in the case where the residue is volatile, or because an optional step of extracting this residue is carried out in the method for manufacturing the composition.

In one embodiment, the phenol-aldehyde resin not yet having crosslinked, the rubber composition comprises at least one aromatic polyphenol derivative according to the invention and at least one aldehyde.

Preferably, in this embodiment, the composition is in the uncured state, i.e. unvulcanized.

The rubber composition may preferably be used in the tyre in the form of a layer. Layer is intended to mean any three-dimensional element having any shape and any thickness, especially in the form of a sheet or strip or other element having any cross section, for example rectangular or triangular.

Aldehyde at the Heart of the Phenol-Aldehyde Resin

The composition comprises one or more aldehyde(s).

Advantageously, the or at least one aldehyde is an aromatic aldehyde.

Such an aldehyde is very advantageous. Specifically, the Applicants have discovered, during their research, that the aromatic aldehyde makes it possible to avoid the production of formaldehyde, unlike conventional methylene donors. Specifically, the combination of phenolic resin conventionally used as methylene acceptor with HMT or H3M as methylene donor in the prior art produces formaldehyde during the vulcanization of the rubber composition. However, it is desirable to reduce, or even eliminate in the long run, formaldehyde from rubber compositions due to the environmental impact of these compounds and the recent developments in regulations, especially European regulations, relating to this type of compound.

Moreover, such an aromatic aldehyde is very stable, which limits the risks of degradation, especially by oxidation.

An aromatic aldehyde is a compound containing at least one aromatic ring, this aromatic ring bearing at least one (one or more) aldehyde function.

Preferably, the aromatic aldehyde is selected from the group consisting of 1,3-benzenedicarboxaldehyde, 1,4-benzenedicarboxaldehyde and an aldehyde of formula (A):

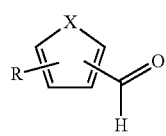
(A)

in which:
X comprises N, S or O,
R represents —H or —CHO,
and the mixtures of these compounds.

The aldehyde is preferentially of general formula (A'):

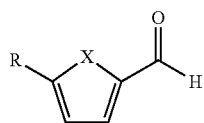
(A')

Even more preferentially, R represents —CHO.

According to a preferential embodiment, X represents O.

In a variant of the aldehyde of general formula (A), X represents O and R represents —H. The aldehyde used is then of formula (Ba):

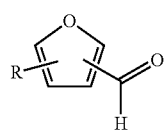
(Ba)

In a variant of the aldehyde of general formula (A'), X represents O and R represents —H. The aldehyde used is then furfuraldehyde and is of formula (B'a):

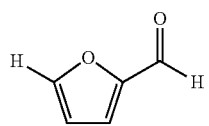
(B'a)

In another variant of the aldehyde of general formula (A), X represents O and R represents —CHO. The aldehyde used is then of formula (Bb):

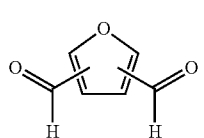
(Bb)

In another variant of the aldehyde of general formula (A'), X represents O and R represents —CHO. The aldehyde used is then 2,5-furandicarboxaldehyde and is of formula (B'b):

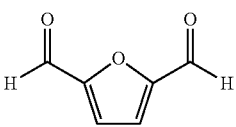
(B'b)

In another embodiment, X comprises N.

In a variant of the aldehyde of general formula (A), X represents NH. The aldehyde used is of formula (Ca):

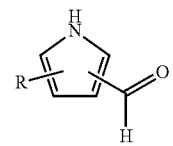
(Ca)

In a variant of the aldehyde of general formula (A'), X represents NH. The aldehyde used is of formula (C'a):

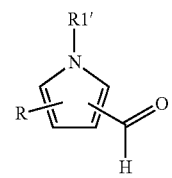
(C'a)

R preferably represents —CHO in the variant of the aldehyde of formula (C'a) and the aldehyde obtained is then 2,5-1H-pyrroledicarboxaldehyde.

In another variant of the aldehyde of general formula (A), X represents NR1' with R1' representing a radical selected from the group consisting of alkyl, aryl, arylalkyl, alkylaryl and cycloalkyl radicals. The aldehyde used is of formula (Cb):

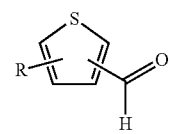
(Cb)

In another embodiment, X comprises S.

In a variant of the aldehyde of general formula (A), X represents S. The aldehyde used is of formula (Da):

(Da)

In a variant of the aldehyde of general formula (A'), X represents S. The aldehyde used is of formula (D'a):

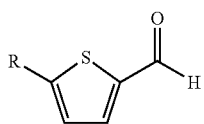

(D'a)

R preferably represents —CHO in the variant of the aldehyde of formula (IV'a) and is then 2,5-thiophenedicarboxaldehyde.

In another variant of the aldehyde of general formula (A), X represents SR2' with R2' representing a radical selected from the group consisting of alkyl, aryl, arylalkyl, alkylaryl and cycloalkyl radicals. The aldehyde used is of formula (Db):

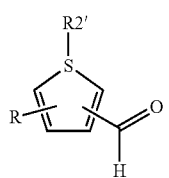

(Db)

In yet another variant of the aldehyde of general formula (A), X represents R3'-S—R2' with R2' and R3' representing, each independently of one another, a radical selected from the group consisting of alkyl, aryl, arylalkyl, alkylaryl and cycloalkyl radicals. The aldehyde used is of formula (Dc):

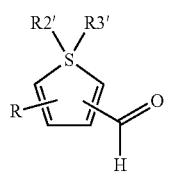

(Dc)

In yet another variant of the aldehyde of general formula (A), X represents S=O. The aldehyde used is of formula (Dd):

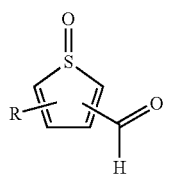

(Dd)

In yet another variant of the aldehyde of general formula (A), X represents O=S=O. The aldehyde used is of formula (De):

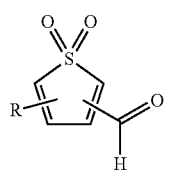

(De)

Among the different embodiments described above, preference will be given to the embodiments and variants in which X represents NH, S or O. In these embodiments and variants, it will be possible to have R representing —H or —CHO and preferably R representing —CHO. In these embodiments and variants, R will preferentially be in the 5 position and the —CHO group will preferentially be in the 2 position on the aromatic ring (general formula (A')).

Thus, more preferentially, the aromatic aldehyde is selected from the group consisting of 1,4-benzenedicarboxaldehyde, furfuraldehyde, 2,5-furandicarboxaldehyde and the mixtures of these compounds.

The composition is preferably devoid of formaldehyde.

When the phenol-aldehyde resin is based on several aldehydes, at least one of which is an aromatic aldehyde as described above, each aldehyde other than each aromatic aldehyde as described above is preferentially different from formaldehyde. The composition is then also preferably devoid of formaldehyde.

In other words and preferably, the or each aldehyde of the phenol-aldehyde resin is different from formaldehyde.

"Devoid of formaldehyde" is intended to mean that the content by weight of formaldehyde, by total weight of the aldehyde or aldehydes, is strictly less than 1%.

In some embodiments, the composition can comprise formaldehyde. Preferably, the composition then comprises a content by weight of formaldehyde, by total weight of the aldehyde or aldehydes, of less than or equal to 10%, preferably to 5% and more preferentially to 2%.

Rubber Composite

The rubber composite is reinforced with at least one reinforcing element embedded in the rubber composition comprising a phenol-aldehyde resin based on an aromatic polyphenol derivative according to the invention.

This rubber composite can be prepared according to a process comprising at least the following steps:

during a first step, combining at least one reinforcing element with a rubber composition (or elastomer; the two terms are synonymous) to form a rubber composite reinforced with the reinforcing element;

then, during a second step, crosslinking by curing, for example by vulcanizing, preferably under pressure, the composite formed in this way.

Among reinforcing elements, mention may be made of textile, metallic, or textile-metallic hybrid reinforcing elements.

"Textile" is intended to mean, in a manner well known to those skilled in the art, any material made of a substance other than a metallic substance, whether natural or synthetic, which is capable of being transformed into thread or fibre by any appropriate transformation process. Mention may be made, for example, without the examples below being limiting, of a polymer spinning process, such as, for example, melt spinning, solution spinning or gel spinning.

This textile material may consist of a thread or fibre, or also of a fabric produced from threads or fibres, for example a woven fabric with warp threads and weft threads, or else a twill fabric with cross threads.

This textile material of the invention is preferably selected from the group consisting of monofilaments (or individual threads), multifilament fibres, assemblies of such threads or fibres, and mixtures of such materials. It is more particularly a monofilament, a multifilament fibre or a folded yarn.

The term thread or fibre is generally intended to mean any elongate element of great length relative to its cross section, regardless of the shape, for example circular, oblong, rectangular, square, or even flat, of this cross section, it being possible for this thread to be straight or not straight, for example twisted or wavy. The largest dimension of its cross section is preferentially less than 5 mm, more preferentially less than 3 mm.

This thread or fibre may take any known form. For example, it may be an individual monofilament of large diameter (for example and preferably equal to or greater than 50 μm), a multifilament fibre (consisting of a plurality of elementary filaments of small diameter, typically less than 30 μm), a textile folded yarn or cord formed from several textile fibres or monofilaments twisted or cabled together, or else an assembly, group or row of threads or fibres, such as, for example, a band or strip comprising several of these monofilaments, fibres, folded yarns or cords grouped together, for example aligned along a main direction, whether straight or not.

The textile materials may be made of organic, polymeric or inorganic substances.

Mention will be made, as examples of inorganic substances, of glass or carbon.

The invention is preferentially implemented with materials made of polymeric substance, of both the thermoplastic and non-thermoplastic type.

Mention will be made, as examples of polymeric substances of the non-thermoplastic type, for example, of aramid (aromatic polyamide) and cellulose, both natural and artificial, such as cotton, rayon, flax or hemp.

Mention will preferentially be made, as examples of polymeric substances of the thermoplastic type, of aliphatic polyamides and of polyesters. Mention may especially be made, among the aliphatic polyamides, of the polyamides 4-6, 6, 6-6, 11 or 12. Mention may be made, among polyesters, for example, of PET (polyethylene terephthalate), PEN (polyethylene naphthalate), PBT (polybutylene terephthalate), PBN (polybutylene naphthalate), PPT (polypropylene terephthalate), and PPN (polypropylene naphthalate).

By definition, metallic is intended to mean one or more threadlike elements made up predominantly (that is to say more than 50% of its weight) or entirely (100% of its weight) of a metallic material. The metallic material is preferably steel, more preferentially perlitic (or ferritic-perlitic) carbon steel advantageously comprising between 0.4% and 1.2% by weight of carbon.

The metallic reinforcing element may be a monofilament, a cord comprising several metallic monofilaments or a multistrand rope comprising several cords, then referred to as strands.

In the preferred case in which the reinforcing element comprises several metallic monofilaments or several strands, the metallic monofilaments or the strands are assembled by twisting or braiding. It is recalled that there are two possible techniques for assembly:

either by twisting: the metallic monofilaments or the strands undergo both a collective twist and an individual twist about their own axis, thereby generating an untwisting torque on each of the monofilaments or strands;

or by braiding: the metallic monofilaments or the strands only undergo a collective twist and do not undergo an individual twist about their own axis.

The reinforcing element optionally comprises several monofilaments and is of the rubberized in situ type, that is to say that the reinforcing element is rubberized from the inside, during the actual manufacture thereof, by a filling rubber. Such metallic threadlike elements are known to those skilled in the art. The composition of the filling rubber may be identical, or not identical, to the rubber composition in which the reinforcing element is embedded.

Tyre

Such tyres are, for example, those intended to be fitted onto motor vehicles of the passenger type, SUVs ("Sport Utility Vehicles"), two-wheel vehicles (especially bicycles and motorcycles), aircraft, or industrial vehicles chosen from vans, "heavy-duty" vehicles—that is to say underground trains, buses, heavy road transport vehicles (lorries, tractors, trailers), off-road vehicles, such as agricultural or civil engineering machines—and other transport or handling vehicles.

By way of example, appended FIG. 1 represents highly schematically (without being true to a specific scale) a radial section of a tyre in accordance with the invention for a vehicle of the heavy-duty type.

This tyre 1 has a crown 2 reinforced by a crown reinforcement or belt 6, two sidewalls 3 and two beads 4, each of these beads 4 being reinforced with a bead wire 5. The crown 2 is surmounted by a tread, not represented in this diagrammatic figure. A carcass reinforcement 7 is wound around the two bead wires 5 in each bead 4, the turn-up 8 of this reinforcement 7 being, for example, positioned towards the outside of the tyre 1, which is here represented fitted onto its wheel rim 9. The carcass reinforcement 7 is, in a way known per se, composed of at least one ply reinforced by "radial" cords, for example made of metal, that is to say that these cords are positioned virtually parallel to one another and extend from one bead to the other so as to form an angle of between 80° and 90° with the median circumferential plane (plane perpendicular to the axis of rotation of the tyre which is located halfway between the two beads 4 and passes through the middle of the crown reinforcement 6).

This tyre 1 of the invention has, for example, the characteristic that at least a crown reinforcement 6 and/or its carcass reinforcement 7 comprises a rubber composition comprising a phenol-aldehyde resin based on an aromatic polyphenol derivative according to the invention.

Method for Manufacturing the Aromatic Polyphenol Derivative

The aromatic polyphenol derivative as defined above is manufactured by means of a method in which the following are reacted:

an aromatic polyphenol comprising at least one aromatic ring bearing at least two —OH hydroxyl functions in the meta position relative to one another, the two positions ortho to at least one of the —OH hydroxyl functions being unsubstituted, and a compound of formula LG-Si($R_1R_2R_3$) with $R_1$, $R_2$, $R_3$ representing, independently of one another, a hydrocarbon-based radical or a substituted hydrocarbon-based radical and LG representing a leaving group.

The conditions of the reaction between the aromatic polyphenol and the compound of formula LG-Si($R_1R_2R_3$) are well known to a person skilled in the art. Thus, for example, the method according to the invention is carried out by firstly reacting, in an organic solvent, the aromatic polyphenol with a base, more preferentially an organic base, then by introducing the compound of formula LG-Si($R_1R_2R_3$) into the reaction mixture. Depending on the $R_1$, $R_2$ and $R_3$ groups and on the aromatic polyphenol, the reaction is carried out between 20° C. and 50° C. for several hours, for example between 1 hour and 10 hours.

In one embodiment of the method according to the invention described above, the leaving group LG represents a halogen. It is recalled that halogens correspond to the elements F, Cl, Br and I.

More preferentially, LG represents chlorine.

Method for Manufacturing the Rubber Composition

The manufacturing method described above and below makes it possible to manufacture the rubber composition comprising a phenol-aldehyde resin based on an aromatic polyphenol derivative according to the invention.

The rubber composition may be manufactured in suitable mixers, using two successive preparation phases well known to those skilled in the art:

a first phase of thermomechanical working or kneading ("non-productive" phase) at high temperature, up to a maximum temperature of between 110° C. and 190° C., preferably between 130° C. and 180° C., followed by a second phase of mechanical working ("productive" phase) down to a lower temperature, typically of less than 110° C., for example between 40° C. and 100° C., during which finishing phase the crosslinking system is incorporated.

In a first embodiment, the method comprises the following steps:

incorporating, in an elastomer, during a first step, a reinforcing filler, everything being kneaded thermomechanically until a maximum temperature of between 110° C. and 190° C. is reached;

cooling the combined mixture to a temperature below 110° C.;

then incorporating, during a second step, a crosslinking system, the aromatic polyphenol derivative according to the invention and the aldehyde;

kneading everything at a temperature below 110° C.

By way of example, the non-productive phase is carried out in a single thermomechanical step during which firstly all the necessary base constituents (diene elastomer, reinforcing filler, etc.) are introduced into an appropriate mixer, such as a standard internal mixer, then secondly, for example after kneading for one to two minutes, the other additives, optional additional agents for covering the filler or optional additional processing aids, with the exception of the crosslinking system, the aromatic polyphenol derivative according to the invention and the aldehyde, are introduced. The total kneading time, in this non-productive phase, is preferably between 1 and 15 min.

After cooling the mixture thus obtained, the crosslinking system, the aldehyde and the aromatic polyphenol derivative according to the invention are then incorporated in an external mixer, such as an open mill, maintained at a low temperature (for example between 40° C. and 100° C.). The combined mixture is then mixed (productive phase) for a few minutes, for example between 2 and 15 min.

The composition thus obtained in the uncured state can subsequently be shaped, for example calendered, for example in the form of a sheet or of a slab, especially for laboratory characterization, or else extruded, for example in order to form a rubber profiled element used in the manufacture of a tyre.

Then, after an optional step of assembling together several compositions formed as plies or strips in the form of a composite or an uncured tyre blank, a step of vulcanizing the composition, the composite or the blank is carried out during which the phenol-aldehyde resin based on the aromatic polyphenol derivative according to the invention and on the aldehyde is crosslinked. The vulcanization step is carried out at a temperature greater than or equal to 120° C., preferably greater than or equal to 140° C. The composition is obtained in the cured state.

In a second embodiment, the method comprises the following steps:

incorporating, in an elastomer, during a first step, a reinforcing filler, the derivative of the aromatic polyphenol and the aldehyde, everything being kneaded thermomechanically until a maximum temperature of between 110° C. and 190° C. is reached;

cooling the combined mixture to a temperature below 110° C.;

subsequently incorporating, during a second step, a crosslinking system;

kneading everything at a temperature below 110° C.

The invention and its advantages will be easily understood in the light of the exemplary embodiments which follow.

EXEMPLARY EMBODIMENTS OF THE INVENTION AND COMPARATIVE TESTS

These tests demonstrate that:

the stiffness of the rubber composition comprising a phenol-aldehyde resin based on an aromatic polyphenol derivative according to the invention is greatly increased compared to a rubber composition devoid of reinforcing resin;

the stiffness of the rubber composition comprising a phenol-aldehyde resin based on an aromatic polyphenol derivative according to the invention may be improved compared to a rubber composition using a conventional reinforcing resin based on a methylene acceptor with HMT or H3M as methylene donor;

the stiffness retention of the rubber composition according to the invention at high temperatures, in particular for temperatures ranging up to 150° C., is greater than that of the rubber compositions devoid of reinforcing resin and equivalent to, or even greater than, in certain embodiments, that of the conventional rubber compositions that comprise HMT or H3M methylene donors;

there is a delay phase during the crosslinking of the phenol-aldehyde resin based on an aromatic polyphenol derivative according to the invention making it possible to avoid the premature crosslinking of the resin relative to a phenol-aldehyde resin crosslinked directly starting from the aromatic polyphenol and the aldehyde;

the phenol-aldehyde resin based on an aromatic polyphenol derivative according to the invention and on a preferentially aromatic aldehyde is devoid of formaldehyde and does not generate any formaldehyde during its formation.

For this purpose, several rubber compositions, denoted hereinafter T0, T1 and T2 and I1 to I3 were prepared as indicated above and are summarized in the appended Table 1 below.

All the compositions T0 to T2 and I1 to I3 have the following shared portion in their formulations (expressed in phr, parts by weight per hundred parts of elastomer): 100 phr of natural rubber, 75 phr of carbon black N326, 1.5 phr of N-(1,3-dimethylbutyl)-N-phenyl-para-phenylenediamine, 1.5 phr of stearic acid, 5 phr of ZnO, 1 phr of N-(tert-butyl)-2-benzothiazolesulfamide and 2.5 phr of insoluble sulfur 20H.

The composition T0 does not comprise any reinforcing resin added to this shared portion.

In addition to the shared portion, the composition T1 comprises a reinforcing resin based on hexamethylenetetramine (1.6 phr) and on a pre-condensed phenolic resin (4 phr). The composition T1 represents a conventional composition of the prior art, having greater stiffness than that of the composition T0.

In addition to the shared portion, the composition T2 comprises a phenol-aldehyde resin based on phloroglucinol and on 1,4-benzenedicarboxaldehyde. The composition T2 comprises 7 phr of phloroglucinol and 14 phr of 1,4-benzenedicarboxaldehyde.

In addition to the shared portion, each composition I1 to I3 comprises a phenol-aldehyde resin based on an aromatic polyphenol derivative according to the invention and on an aldehyde, preferably an aromatic aldehyde, which are indicated in Table 1 in 1 (aromatic polyphenol derivative according to the invention)/2 (aldehyde) molar proportions, and with, in each composition I1 to I3, 14 phr of the aldehyde.

Each aromatic polyphenol derivative according to the invention in each composition I1 to I3 comprises at least one aromatic ring bearing at least two —O—Z groups in the meta position relative to one another, the two positions ortho to at least one of the —O—Z groups being unsubstituted, and in which each —O—Z group represents an —O—Si($R_1R_2R_3$) group with $R_1$, $R_2$, $R_3$ representing, independently of one another, a hydrocarbon-based radical or a substituted hydrocarbon-based radical.

Aromatic Polyphenol Derivatives of Compositions I1 to I3

Each aromatic polyphenol derivative according to the invention of the resin of each composition I1 to I3 is selected from the group consisting of the aromatic polyphenol derivatives of formulae (I), (II), (IV) and (V) described above and the mixtures of these aromatic polyphenol derivatives.

Each aromatic polyphenol derivative according to the invention of each composition I1 to I3 comprises a single aromatic ring, in this case a benzene ring, bearing three, and only three, —O—Z groups in the meta position relative to one another.

For the aromatic polyphenol derivatives according to the invention of each composition I1 to I3, the remainder of the aromatic ring is unsubstituted. In particular, the two positions ortho to each —O—Z group are unsubstituted. In the case in point, these are aromatic polyphenol derivatives of general formula (II) obtained from phloroglucinol.

Each aromatic polyphenol derivative according to the invention of each composition I1 to I3 has —O—Z groups that each represent an —O—Si($R_1R_2R_3$) group with $R_1$, $R_2$, $R_3$ representing, independently of one another, a radical selected from the group consisting of alkyl, aryl, arylalkyl, alkylaryl, cycloalkyl and alkenyl radicals. Preferably, each $R_1$, $R_2$, $R_3$ group represents, independently of one another, a radical selected from the group consisting of methyl, ethyl, propyl, phenyl, allyl and vinyl radicals and more preferentially still a radical selected from the group consisting of methyl, ethyl, propyl, butyl, allyl and vinyl radicals.

The aromatic polyphenol derivative according to the invention of composition I1 is such that $R_1$=$R_2$=$R_3$=$CH_3$ and has the following formula (5):

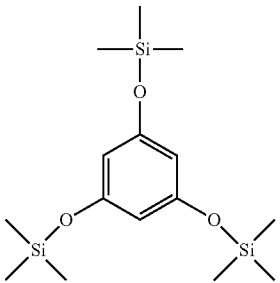

(5)

Figure 2A:
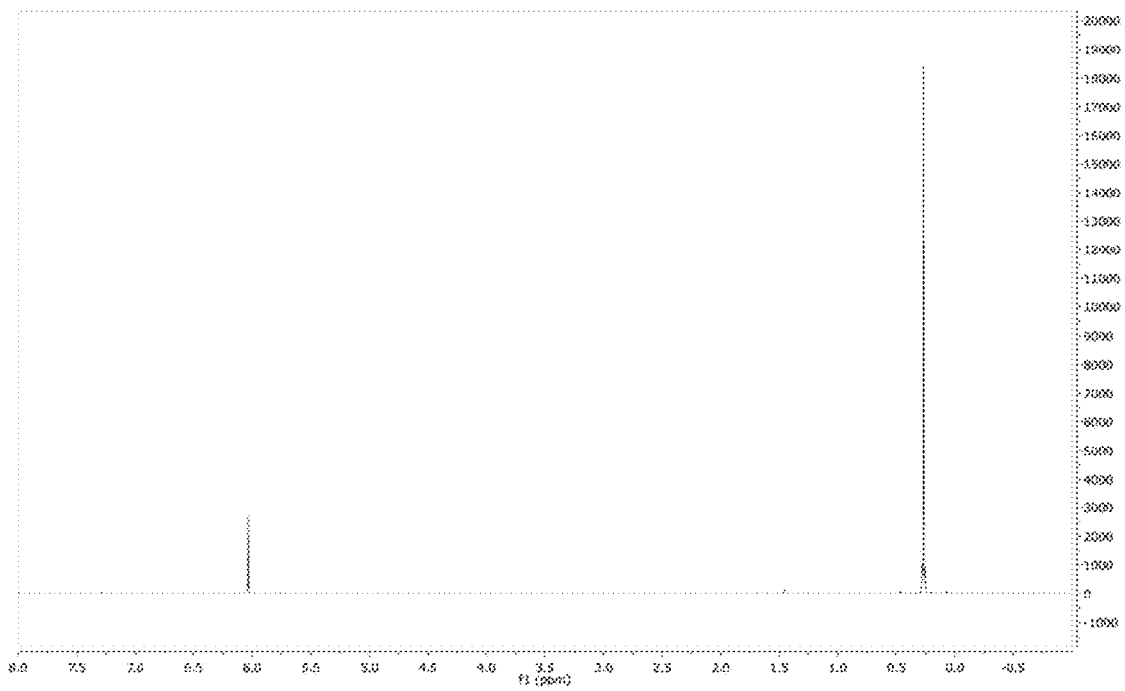
FIG. 2A is the $^1$HNMR spectrum of derivative (5)
Figure 2B:
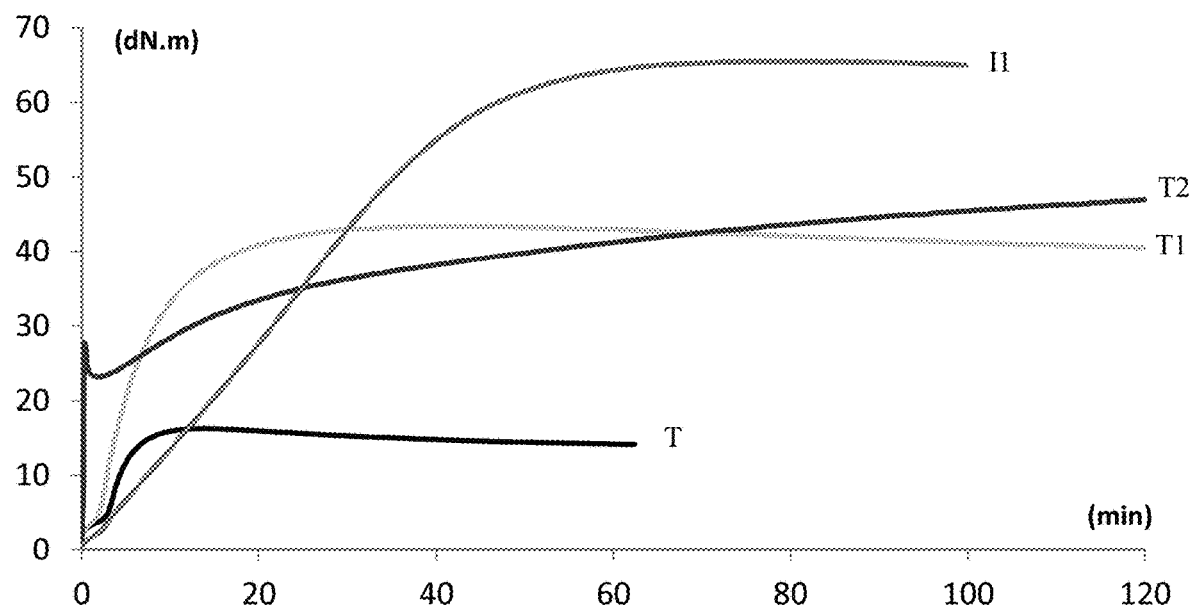
FIG. 2B is a representation of the change in the rheometric torque of related compositions of the present invention.

The aromatic polyphenol derivative (5) is prepared from phloroglucinol (CAS 108-73-6) and from trimethylsilyl chloride (CAS 75-77-4) (LG-Si($R_1R_2R_3$)) with LG=Cl and $R_1$=$R_2$=$R_3$=methyl) in the presence of an organic base. Thus, for example, 40 g of phloroglucinol are dissolved in 800 ml of chloroform. Next, 109 g of triethylamine are then added. Next, 107 g of trimethylsilyl chloride ClSi($CH_3$)$_3$ are added dropwise to the reaction medium at ambient temperature. Everything is left stirring at ambient temperature for 3 hours. Next, the reaction mixture is acidified with a 37% aqueous solution of hydrochloric acid. Next, it is washed twice with water. The final product is finally recovered after drying over anhydrous sodium sulfate, filtration and evaporation of the solvent. 150 g of the aromatic polyphenol derivative (5) are obtained in the form of a brown liquid. The $^1$H NMR spectrum of the aromatic polyphenol derivative (5) is represented in FIG. 2A ($^1$H NMR (CDCl$_3$, 300 MHz): 6.03 (3H, s), 0.27 (27H, s)).

The aromatic polyphenol derivative of composition I2 is such that $R_1$=$R_2$=$CH_3$, $R_3$=CH=$CH_2$ and has the following formula (6):

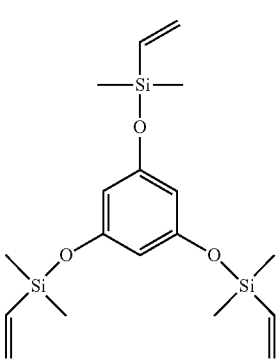

(6)

Figure 3A:
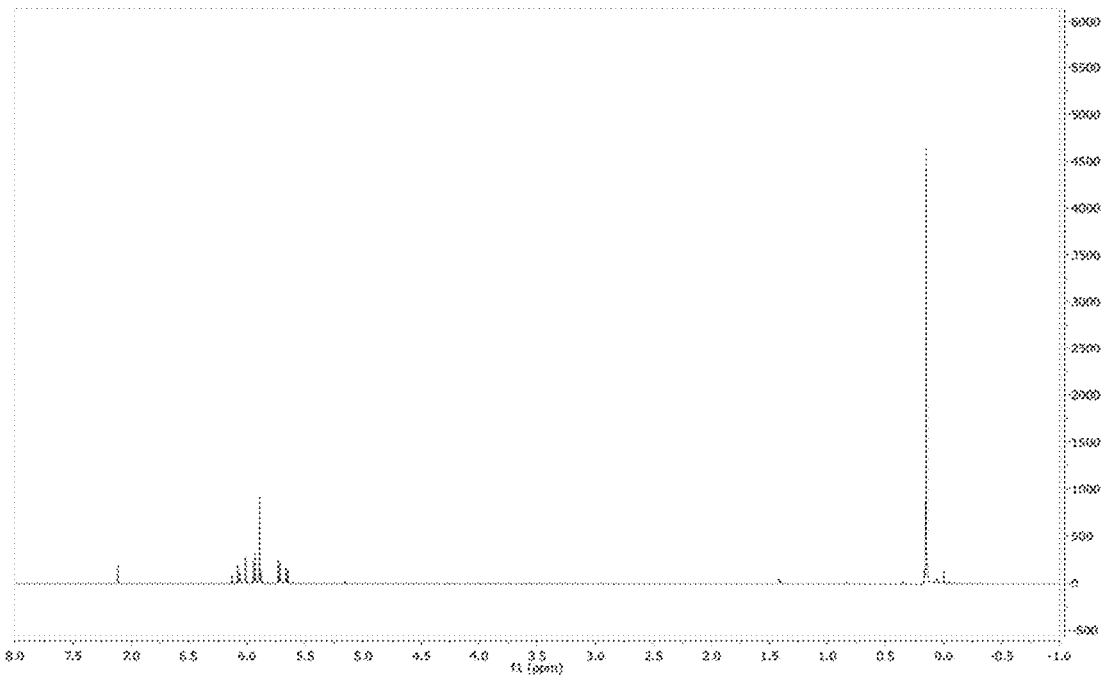
FIG. 3A is the $^1$HNMR spectrum of derivative (6)
Figure 3B:
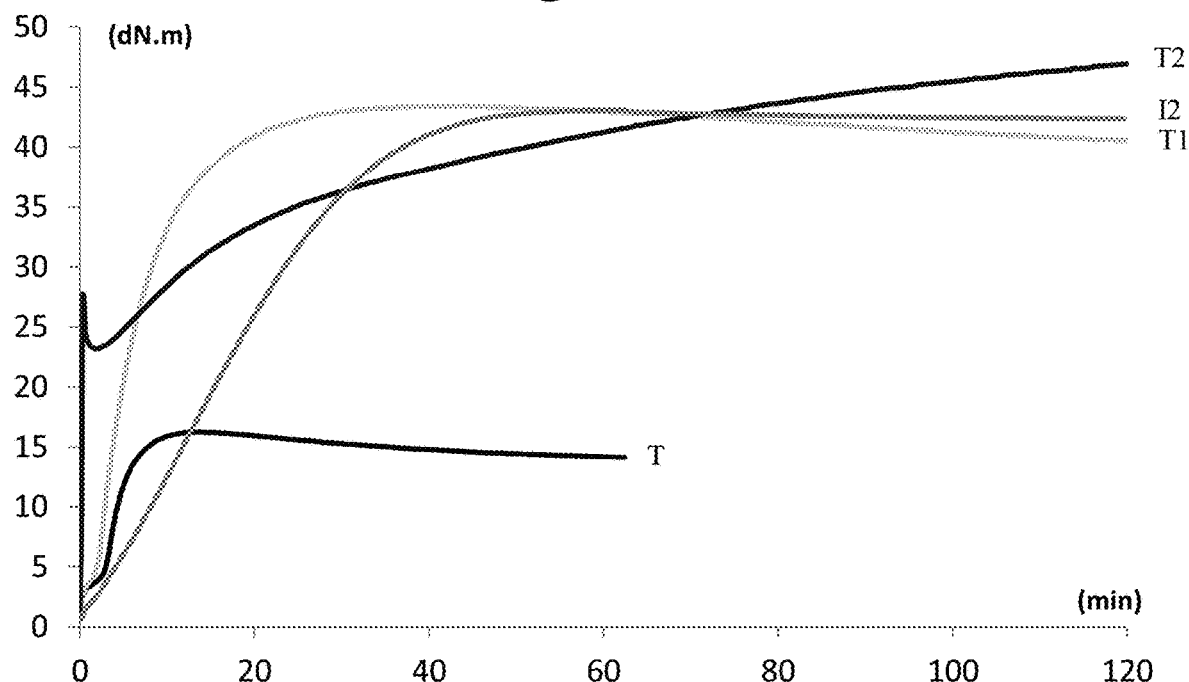
FIG. 3B is a representation of the change in the rheometric torque of related compositions of the present invention.

The aromatic polyphenol derivative (6) is prepared in a similar manner to the aromatic polyphenol derivative (5) from phloroglucinol (CAS 108-73-6) and from dimethylvinylsilyl chloride (CAS 1719-58-0) (LG-Si($R_1R_2R_3$) with LG=Cl and $R_1$=$R_2$=methyl and $R_3$=CH=$CH_2$). The $^1$H NMR spectrum of the aromatic polyphenol derivative (6) is represented in FIG. 3A ($^1$H NMR (CDCl$_3$, 300 MHz): 6.15-5.60 (9H, m), 5.89 (3H, s), 0.15 (18H, s)).

The aromatic polyphenol derivative of composition I3 is such that $R_1$=$CH_3$, $R_2$=$R_3$=$C_6H_6$ and has the following formula (7):

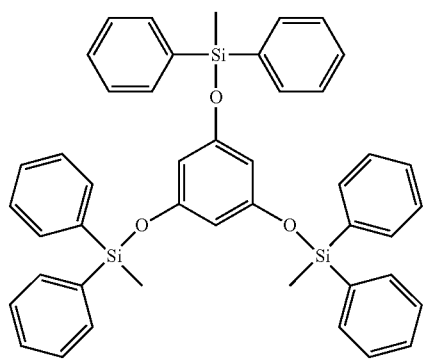

(7)

Figure 4A:
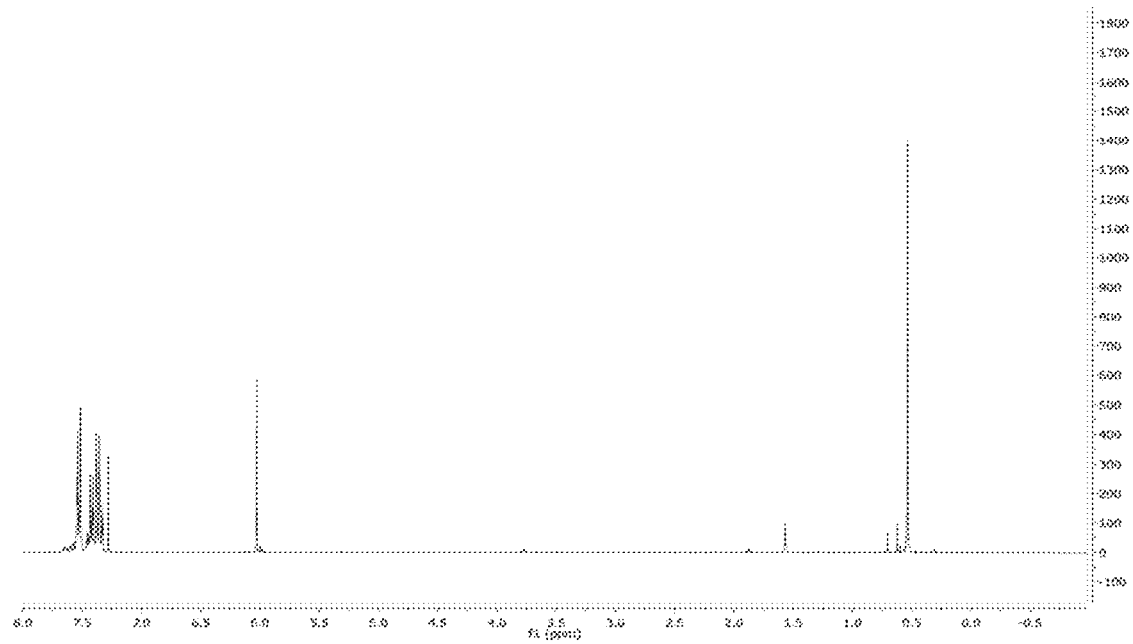
FIG. 4A is the $^1$HNMR spectrum of derivative (7)
Figure 4B:
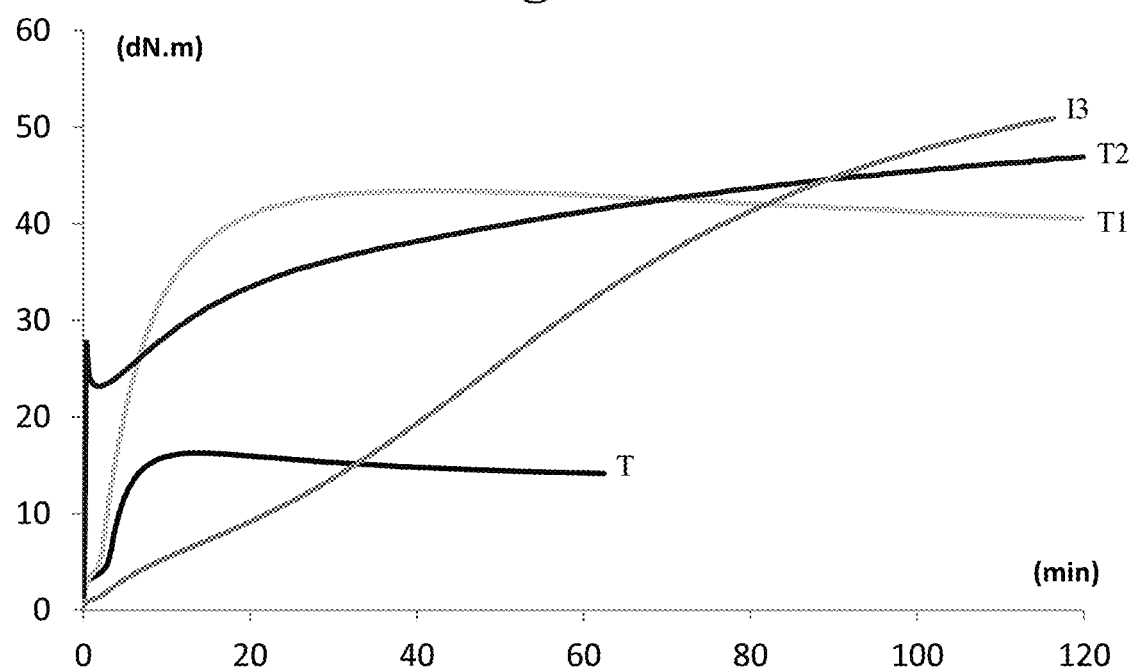
FIG. 4B is a representation of the change in the rheometric torque of related compositions of the present invention.

The aromatic polyphenol derivative (7) is prepared in a similar manner to the aromatic polyphenol derivative (5) from phloroglucinol (CAS 108-73-6) and from methyldiphenylsilyl chloride (CAS 144-79-6) (LG-Si($R_1R_2R_3$) with LG=Cl and $R_1$=methyl and $R_2$=$R_3$=$C_6H_5$). The $^1$H NMR spectrum of the aromatic polyphenol derivative (7) is represented in FIG. 4A ($^1$H NMR (CDCl$_3$, 300 MHz): 7.70-7.30 (30H, m), 6.03 (3H, s), 0.59 (9H, s)).

Aldehyde of Compositions I1 to I3

Each aldehyde of each composition I1 to I3 is a preferentially aromatic aldehyde and is selected from the group consisting of 1,3-benzenedicarboxaldehyde, 1,4-benzenedicarboxaldehyde and an aldehyde of formula (A):

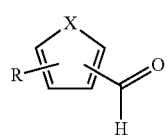

(A)

in which:
X comprises N, S or O,
R represents —H or —CHO,
and the mixtures of these compounds.

In this case, the aldehyde is selected from the group consisting of 1,4-benzenedicarboxaldehyde, furfuraldehyde, 2,5-furandicarboxaldehyde and the mixtures of these compounds. Here, the aldehyde of each composition I1 to I3 is 1,4-benzenedicarboxaldehyde.

Comparative Tests

In a first step, the reinforcing filler was incorporated into an elastomer, everything being kneaded thermomechanically until a maximum temperature of between 110° C. and 190° C. was reached. Then the combined mixture was cooled to a temperature below 110° C. Next, during a second step, the crosslinking system, the phenol, the aromatic polyphenol or the aromatic polyphenol derivative according to the invention and the aldehyde were incorporated. At the end of this second step, the mixture was heated to 150° C. until the maximum rheometric torque was obtained in order to vulcanize the composition and crosslink the phenol-aldehyde resin. Next, the stiffness at 23° C. of the composition was characterized during a tensile test.

Characterization of the Delay Phase and of the Stiffness at High Temperature-Maximum Rheometric Torque The measurements are carried out at 150° C. with an oscillating disc rheometer, according to standard DIN 53529-Part 3 (June 1983). The change in the rheometric torque as a function of the time describes the change in the stiffening of the composition following vulcanization and crosslinking of the phenol-aldehyde resin. From the change in the rheometric torque, the presence of a delay phase is determined when the increase in the rheometric torque, over 10 minutes, of the composition tested is lower than the increase in the rheometric torque, over 10 minutes, of a control composition comprising the corresponding aromatic polyphenol and the same aldehyde, here the composition T2. The presence of such a delay phase is indicated in Table 1. Each curve that represents the change in the rheometric torque respectively of compositions I1 to I3 and also those that represent the change in the rheometric torque of compositions T0, T1 and T2 have been represented in FIGS. 2B to 4B.

The higher the maximum rheometric torque Cmax, the more the composition has a stiffness which can be maintained at high temperature.

Characterization of the Stiffness at 23° C.—Tensile Test

These tests make it possible to determine the elasticity stresses and the properties at break. Unless indicated otherwise, they are carried out in accordance with standard ASTM D 412, 1998 (test specimen C). The "nominal" secant moduli (or apparent stresses, in MPa) at 10% elongation (denoted "MA10") are measured in second elongation (i.e., after an accommodation cycle). All these tensile measurements are carried out under normal temperature and relative humidity conditions, according to standard ASTM D 1349, 1999, and are reported in Table 1.

Firstly, the results from Table 1 show that the use of an aromatic polyphenol and of an aldehyde in the control composition T2 makes it possible to obtain a stiffness at 23° C. that is much higher than that of a composition devoid of reinforcing resin (T0) but also than that of a composition comprising a reinforcing resin of the prior art (T1). However, the composition T2 has no delay phase so that the phenol-aldehyde resin of the composition T2 crosslinks prematurely.

In addition to its delay phase, each composition according to the invention I1 to I3 has a stiffness at 23° C. that is equivalent to or even greater than that of the composition T1. Furthermore, unlike T1, none of the compositions I1 to I3 produces formaldehyde during the vulcanization thereof.

Each composition I1 to I3 has a delay phase and a stiffness which, although lower than that of the composition T2 in certain examples described, is sufficient to enable a reinforcement of the rubber composition. Moreover, this stiffness may be increased by modifying other parameters such as the contents of aromatic polyphenol derivative according to the invention and aldehyde used.

Each composition I1 to I3 has an improved stiffness retention at high temperatures (Cmax) compared to the retention of composition T0. Furthermore, the compositions I1 to I3 have a stiffness retention at high temperatures (Cmax) that is at least equal to (I2) or even significantly higher than (I1 and I3) that of the composition T1.

It will also be noted that the delay phase and the stiffness at 23° C. may be selected as a function of the application by varying the —O—Z group and in particular the $R_1$, $R_2$ and $R_3$ groups.

The invention is not limited to the embodiments described above.

In other embodiments not present in Table 1, aromatic polyphenol derivatives comprising several aromatic rings, for example benzene rings, could be envisaged, at least two of these rings each bearing at least two —O—Z groups in the meta position relative to one another. The two positions ortho to at least one of the —O—Z groups of each aromatic ring are unsubstituted.

Use could be made of an aromatic polyphenol derivative comprising at least one aromatic ring bearing at least two —O—Z groups in the meta position relative to one another, the two positions ortho to at least one of the —O—Z groups being unsubstituted, and in which each —O—Z group represents an —O—Si($R_1R_2R_3$) group with $R_1$, $R_2$, $R_3$ representing, independently of one another, a hydrocarbon-based radical or a substituted hydrocarbon-based radical by using it to generate a delay phase during the crosslinking of a phenol-aldehyde resin based on the aromatic polyphenol derivative and on an aldehyde, independently of the use thereof for the manufacture of a phenol-aldehyde resin for reinforcing a rubber composition.

The characteristics of the aromatic polyphenol derivative and of the aldehyde described above also apply to this use for generating a delay phase during the crosslinking of the phenol-aldehyde resin.

Use could be made, in certain embodiments, of an aromatic polyphenol derivative comprising at least one aromatic ring bearing at least two —O—Z groups in the meta position relative to one another, the two positions ortho to at least one of the —O—Z groups being unsubstituted, and in which each —O—Z group represents an —O—Si($R_1R_2R_3$) group with $R_1$, $R_2$, $R_3$ representing, independently of one another, a hydrocarbon-based radical or a substituted hydrocarbon-based radical by using it in a phenol-aldehyde resin to maintain the stiffness of a rubber composition with the increase in the temperature, independently of the use thereof for the manufacture of a phenol-aldehyde resin for reinforcing a rubber composition.

The characteristics of the aromatic polyphenol derivative and of the aldehyde described above also apply to this use in a phenol-aldehyde resin for maintaining the stiffness of the rubber composition with the increase in the temperature.

The invention claimed is:

1. A method for the manufacture of a phenol-aldehyde resin for reinforcing a rubber composition comprising the steps of:
mixing at least one aldehyde and an aromatic polyphenol derivative comprising at least one aromatic ring bearing at least two —O—Z groups in the meta position relative to one another, the two positions ortho to at least one of the —O—Z groups being unsubstituted, and in which each —O—Z group represents an —O—Si($R_1R_2R_3$) group with $R_1$, $R_2$, $R_3$ representing, independently of one another, a hydrocarbon-based radical or a substituted hydrocarbon-based radical; and
crosslinking the aromatic polyphenol derivative and the at least one aldehyde to produce the phenol-aldehyde resin.

2. The method according to claim 1, wherein the crosslinking step occurs after a delay phase generated by the aromatic polyphenol derivative.

3. The method according to claim 1, wherein using the aromatic polyphenol derivative in a phenol-aldehyde resin maintains stiffness of a rubber composition with an increase in temperature.

4. The method according to claim 1, wherein the aldehyde is an aromatic aldehyde.

5. The method according to claim 2, wherein the aromatic aldehyde is selected from the group consisting of 1,3-benzenedicarboxaldehyde, 1,4-benzenedicarboxaldehyde and an aldehyde of formula

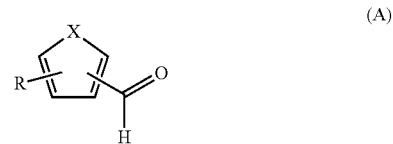

(A)

in which X comprises N, S or O; R represents —H or —CHO, and mixtures thereof.

6. The method according to claim 2, wherein the aromatic aldehyde is selected from the group consisting of 1,4-benzenedicarboxaldehyde, furfuraldehyde, 2,5-furandicarboxaldehyde and mixtures thereof.

TABLE 1

| Composition | Phenol | Methylene donor | Delay phase | MA10 (MPa) | Cmax (dN · m) |
|---|---|---|---|---|---|
| T0 | / | / | / | 7.4 | 16 |
| T1 | SRF resin (1) | Hexamethylenetetramine (2) | No | 16.5 | 43 |

| Composition | Aromatic polyphenol | Aldehyde | Delay phase | MA10 (MPa) | Cmax (dN · m) |
|---|---|---|---|---|---|
| T2 | Phloroglucinol (3) | 1,4-Benzenedicarboxaldehyde (4) | No | 33.5 | 46 |

| Composition | Aromatic polyphenol derivative Z=Si($R_1R_2R_3$) | Aldehyde | Delay phase | MA10 (MPa) | Cmax (dN · m) |
|---|---|---|---|---|---|
| I1 | $R_1$=$R_2$=$R_3$=$CH_3$ (5) | 1,4-Benzenedicarboxaldehyde (4) | Yes | 24.9 | 65 |
| I2 | $R_1$=$R_2$=$CH_3$, $R_3$=CH=$CH_2$ (6) | 1,4-Benzenedicarboxaldehyde (4) | Yes | 23.8 | 43 |
| I3 | $R_1$=$CH_3$,$R_2$=$R_3$=$C_6H_5$ (7) | 1,4-Benzenedicarboxaldehyde (4) | Yes | 16.6 | 50 |

(1) Hexamethylenetetramine (from Sigma-Aldrich; purity of ≥99%);
(2) Pre-condensed resin SRF 1524 (from Schenectady; diluted to 75%);
(3) Phloroglucinol (from Alfa Aesar; purity of 99%);
(4) 1,4-Benzenedicarboxaldehyde (from ABCR; purity of 98%).

7. The method according to claim 1, wherein each $R_1$, $R_2$, $R_3$ group represents, independently of one another, a radical selected from the group consisting of alkyl, aryl, arylalkyl, alkylaryl, cycloalkyl and alkenyl radicals.

8. The method according to claim 1, wherein each $R_1$, $R_2$, $R_3$ group represents, independently of one another, a radical selected from the group consisting of methyl, ethyl, propyl, phenyl, allyl and vinyl radicals.

9. The method according to claim 1, wherein each $R_1$, $R_2$, $R_3$ group represents, independently of one another, a radical selected from the group consisting of methyl, ethyl, propyl, butyl, allyl and vinyl radicals.

10. The method according to claim 1, wherein the at least one aromatic ring bears three —O—Z groups in the meta position relative to one another.

11. The method according to claim 1, wherein the two positions ortho to each —O—Z group are unsubstituted.

12. The method according to claim 1, wherein the remainder of the at least one aromatic ring is unsubstituted.

13. The method according to claim 1, wherein the aromatic polyphenol derivative comprises several aromatic rings, at least two of these each bearing at least two —O—Z groups in the meta position relative to one another, the two positions ortho to at least one of the —O—Z groups of at least one aromatic ring being unsubstituted.

14. The method according to claim 1, wherein the, or each, aromatic ring is a benzene ring.

15. The method according to claim 1, wherein the aromatic polyphenol derivative is selected from the group consisting of the aromatic polyphenol derivatives (I), (II), (IV), (V), and mixtures thereof:

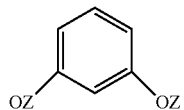
(I)

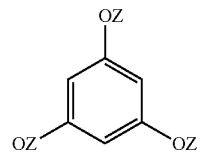
(II)

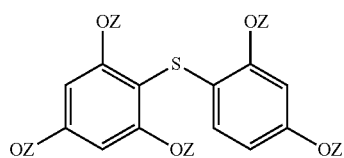
(IV)

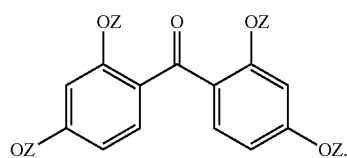
(V)

* * * * *